(12) United States Patent
Church

(10) Patent No.: US 6,520,995 B2
(45) Date of Patent: Feb. 18, 2003

(54) ENDOPROSTHETIC BONE JOINT DEVICES

(75) Inventor: John Christian Tracey Church, Bourne End (GB)

(73) Assignee: BTG International Limited, London (GB)

( * ) Notice: Subject to any disclaimer, the term of this patent is extended or adjusted under 35 U.S.C. 154(b) by 0 days.

(21) Appl. No.: 10/041,508

(22) Filed: Jan. 10, 2002

(65) Prior Publication Data

US 2002/0058998 A1 May 16, 2002

Related U.S. Application Data

(63) Continuation of application No. 07/021,609, filed on Mar. 3, 1987, now Pat. No. 6,352,559, which is a continuation of application No. 06/482,708, filed on Apr. 6, 1983, now abandoned.

(30) Foreign Application Priority Data

Apr. 7, 1982 (GB) ............................................. 8210272

(51) Int. Cl.$^7$ ................................................... A61F 2/32
(52) U.S. Cl. ................................ 623/22.24; 623/22.25; 623/22.15
(58) Field of Search .................... 623/22.21, 22.22, 623/22.23, 22.24, 22.25, 22.26, 22.27, 22.28, 22.29, 22.3, 22.31, 22.32, 22.33, 22.34, 22.35, 22.36, 22.37, 22.38, 22.39, 22.15, 22.17, 22.18, 22.19, 22.2

(56) References Cited

U.S. PATENT DOCUMENTS

| | | | | |
|---|---|---|---|---|
| 3,067,740 A | * | 12/1962 | Haboush | 606/72 |
| 3,584,318 A | * | 6/1971 | Scales et al. | 403/140 |
| 3,683,421 A | * | 8/1972 | Martinie | 277/636 |
| 3,722,002 A | * | 3/1973 | Charnley | 623/22.32 |
| 3,818,512 A | * | 6/1974 | Shersher | 623/22.15 |
| 3,829,904 A | * | 8/1974 | Ling et al. | 623/22.39 |
| 3,894,297 A | * | 7/1975 | Mittelmeier et al. | 623/22.14 |
| 3,903,549 A | * | 9/1975 | Deyerle | 606/73 |
| 3,918,102 A | * | 11/1975 | Eichler | 623/22.39 |

(List continued on next page.)

FOREIGN PATENT DOCUMENTS

| | | |
|---|---|---|
| DE | 51899 | 5/1971 |
| DE | 7104212 | 5/1971 |
| DE | 28 39 661 A1 | 9/1979 |
| DE | 29 50 536 A1 | 7/1981 |
| EP | 0 0650482 | 5/1982 |
| FR | 2099259 | 3/1972 |
| GB | 1292561 | 10/1972 |
| GB | 1371335 | 10/1974 |
| GB | 1534640 | 12/1978 |
| GB | 2007980 | 5/1979 |
| GB | 2013503 | 8/1979 |
| GB | 1573608 | 8/1980 |

OTHER PUBLICATIONS

Consensus Conference, "Total Hip–Joint Replacement in the United States," JAMA, vol. 248, No. 15, Oct. 15, 1982.

(List continued on next page.)

Primary Examiner—David J. Isabella
(74) Attorney, Agent, or Firm—Finnegan, Henderson, Farabow, Garrett and Dunner, LLP

(57) ABSTRACT

An endoprosthetic acetabular component of overall cup form is improved by the provision of an outer part (100; 300; 500) for securement to bone and a plurality of inner parts (200; 400; 600) individually selectively interconnectable with the outer part in like manner but providing a dished articulating surface (203; 403; 603) in respectively different predetermined positions varying in depth and/or inclination. The interconnection is preferably rotatably adjustable relative to the cup mouth, suitably by the provision of mutually complementary indented/detented surface formations (104, 202; 304,402; 505,607) on the parts. The outer part may also be selectable from a range adapted to respectively different manners of securement to bone.

32 Claims, 4 Drawing Sheets

U.S. PATENT DOCUMENTS

Figure 1A:
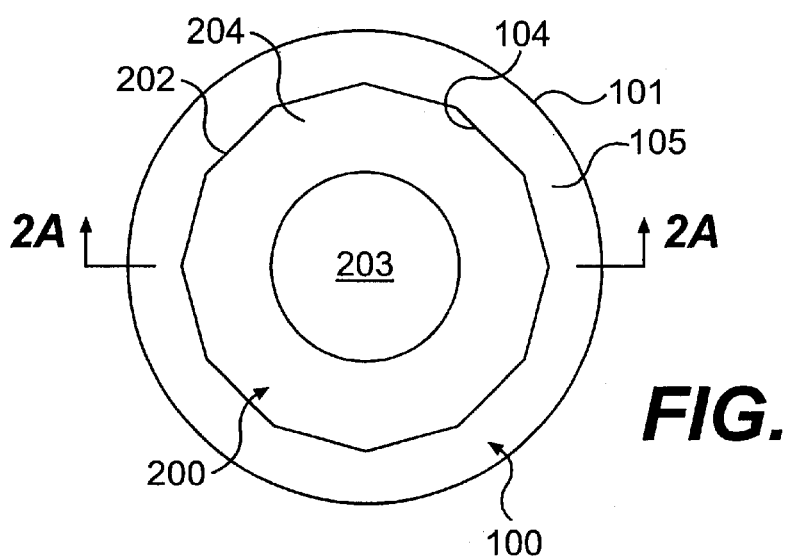

| | | | | |
|---|---|---|---|---|
| RE28,895 E | * | 7/1976 | Noiles | 623/22.31 |
| 3,996,625 A | * | 12/1976 | Noiles | 623/22.15 |
| 4,004,300 A | * | 1/1977 | English | 623/22.17 |
| 4,044,403 A | * | 8/1977 | D'Errico | 623/22.17 |
| 4,051,559 A | * | 10/1977 | Pifferi | 623/22.46 |
| 4,085,466 A | * | 4/1978 | Goodfellow et al. | 623/20.29 |
| 4,172,296 A | * | 10/1979 | D'Errico | 623/22.28 |
| 4,327,449 A | * | 5/1982 | Charnley | 623/22.39 |
| 4,380,090 A | * | 4/1983 | Ramos | 623/22.2 |
| 4,404,691 A | * | 9/1983 | Buning et al. | 623/20.15 |
| 4,795,470 A | * | 1/1989 | Goymann et al. | 623/22.24 |
| 6,352,559 B1 | | 3/2002 | Church | |

OTHER PUBLICATIONS

Harris, William H., M.D., "A New Total Hip Implant," Clinical Orthopaedics and Related Research, No. 81, Nov.–Dec., 1971, pp. 105–113.

Harris, William H., M.D., et al., "Socket Fixation using a Metal–Backed Acetabular Component for Total Hip Replacement," vol. 64–A, No. 5, Jun. 1982, pp. 745–748.

Harris, William H., M.D., et al., "Oh–Harris Protrusio Shell Surgical Technique," Howmedica, Inc., pp. 1–6.

Oh, Indong, M.D., et al., "Design Concepts, Indications, and Surgical Technique for Use of the Protrusio Shell," Clinical Orthopaedics and Related Research, No. 162, Jan. –Feb., 1982, pp. 175–184.

Pipino, F., et al., "A biequatorial acetabular cup for hip prosthesis," Acta Orthopaedica Belgica, Tome 46, Fasc. 1, 1989, pp. 5–13.

Pipino, F., et al., "A biequatorial hip prosthesis," Panminreva Medica, Pan. Med. 25, 1983, pp. 231–239.

Vitallium Harris Total Hip System, Howmedica, Inc., 8 pages (total).

Industrial Invention Patent No. 1095640; Application No. 32723; Year: 1978 (with translation).

Lord, Gerald A., M.D., et al., "An Uncemented Total Hip Replacement," *Clinical Orthopaedics and Related Research*, No. 141, Jun. 1979, pp. 2–16.

Lord, G. A., M.D., and Bancel, P., M.D., "The Madreporic Cementless Total Hip Arthroplasty," *Clinical Orthopaedics and Related Research*, No. 176, Jun. 1983, pp. 67–76.

Woo, Ronald Y., M.D., et al., "Dislocations after Total Hip Arthorplasty," The Journal of Bone and Joint Surgery, vol. 64–A, No. 9, Dec. 1982, pp. 1295–1306.

Advertisement, "Christiansen Trunnion Bearing Hip Joint Replacement System, Benoist Girard & Co.", The Journal of Bone and Joint Surgery, British vol. 59–B, No. 4, Nov. 1977.

* cited by examiner

ENDOPROSTHETIC BONE JOINT DEVICES

This application is a continuation of U.S. application Ser. No. 07/021,609, filed Mar. 3, 1987 (now U.S. Pat. No. 6,352,559), which is a continuation of U.S. application Ser. No. 06/482,708, filed on Apr. 6, 1983 (now abandoned), all of which is incorporated herein by reference.

This invention concerns endoprosthetic bone joint devices and more particularly such devices including a component of overall cup form to replace the acetabulum in the hip joint.

Present day acetabular cup components represent the result of several decades of clinical experience and a yet longer period of trial and development, but the use of such components is nevertheless not without difficulties.

A general difficulty is that an optimum result requires accuracy in the positioning of the component in the pelvis, but such positioning is hindered by the fact that the component has a preset overall geometry while the pelvis will vary in shape between individual patients and so give no absolute spacial frame of reference, and current securement techniques employing fast-curing acrylic bone cement give little scope for adjustment after the component has been first located. The component is usually introduced with a single smooth action to ensure that cement is evenly distributed between it and the bone, and the component is thereafter held steadily, without angular or lateral movement, while the cement is curing in order to avoid the creation of voids or other weaknesses in the securement. In practice therefore the initial positioning of the component is definitive and the attainment of an optimum result accordingly requires skill and care, while the later consequences of failure include undue component wear and/or dislocation.

Even if skill and care are exercised, there is still a difficulty in that optimum positioning of the outer and inner surfaces of the component are respectively determined by the requirements of securement and articulation but, because these requirements can varyingly differ from one patient to another, attainment of both optima is often compromised by a component of preset overall geometry.

An object of the present invention is to reduce these difficulties and to this end there is provided an endoprosthetic acetabular component of overall cup form comprising an outer part and a plurality of inner parts individually selectively co-operable with said outer part, the outer part being adapted for securement to bone, and each inner part being interconnectable with said outer part in like manner and defining a dished articulation surface having a respectively different predetermined position relative to said outer part when connected therewith.

Preferably the inner parts afford a range of articulation surface positions varying in depth and inclination relative to the outer part.

Also, it is preferred that the outer and inner parts are rotatably adjustably interconnectable relative to the mouth of the overall cup form.

The benefit of the proposed device relative to the above-mentioned difficulties is that the outer part can be secured to the bone separately with a fuller attention being paid to the requirements of securement in terms of the geometry and mechanical condition of the bone, and thereafter an appropriate one of the inner parts can be selectively interconnected to locate its dished surface in the position which is judged to be best for the purposes of articulation.

The outer part can take various forms to allow for securement to bone in accordance with established or future techniques. For example, the part can have an outermost surface with a ribbed-and-grooved or other relieved configuration for cooperation with bone cement, or the part can be apertured for the passage of screws therethrough. Indeed the outer part can itself be made available in such different forms interconnectable with the same range of inner parts in like manner to allow a choice of securement technique best suited to a bone when exposed during surgery.

Variation is also possible in the adaptation for interconnection between the outer and inner parts. It is presently preferred that such adaptation involve mutually complementary indented and detented formations on the outer and inner parts. In initially conceived forms of the invention such formations were applied to the interior and exterior surfaces respectively of the outer and inner parts. These initial forms typically involve prismatic surface forms of polygonal or other non-circular cross-sectional shape. However it is now thought advantageous to apply the complementary formations to rim surfaces of the outer and inner parts in order to facilitate associated machining or other fabrication operations. More recently conceived forms of the invention in fact typically involve castellated rim surface formations.

Figure 1B:
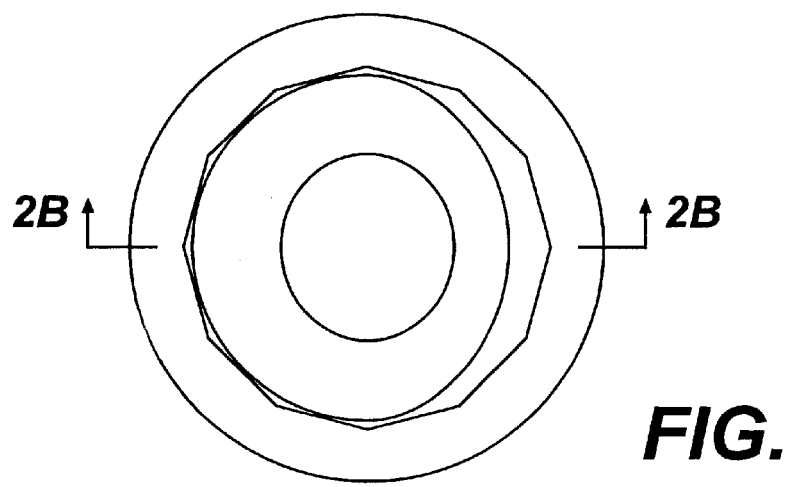
Figure 1C:
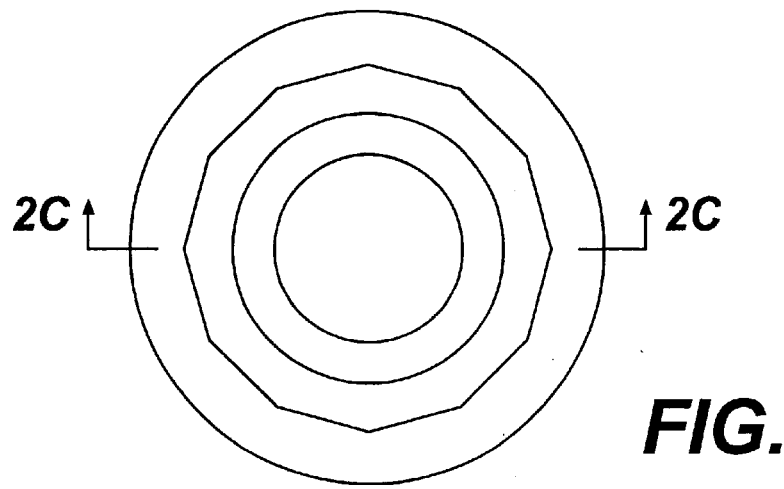
Figure 2A:
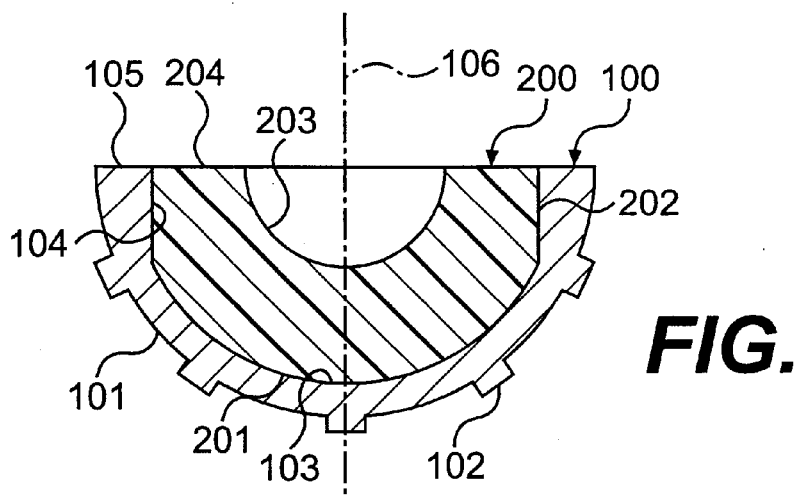
Figure 2B:
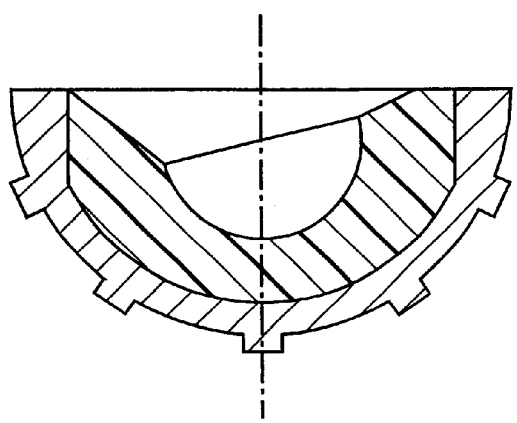
Figure 2C:
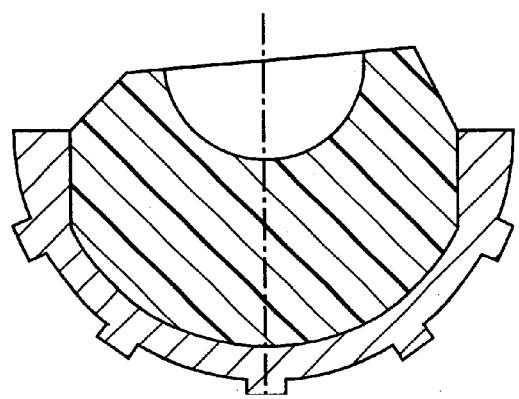
Figure 3:
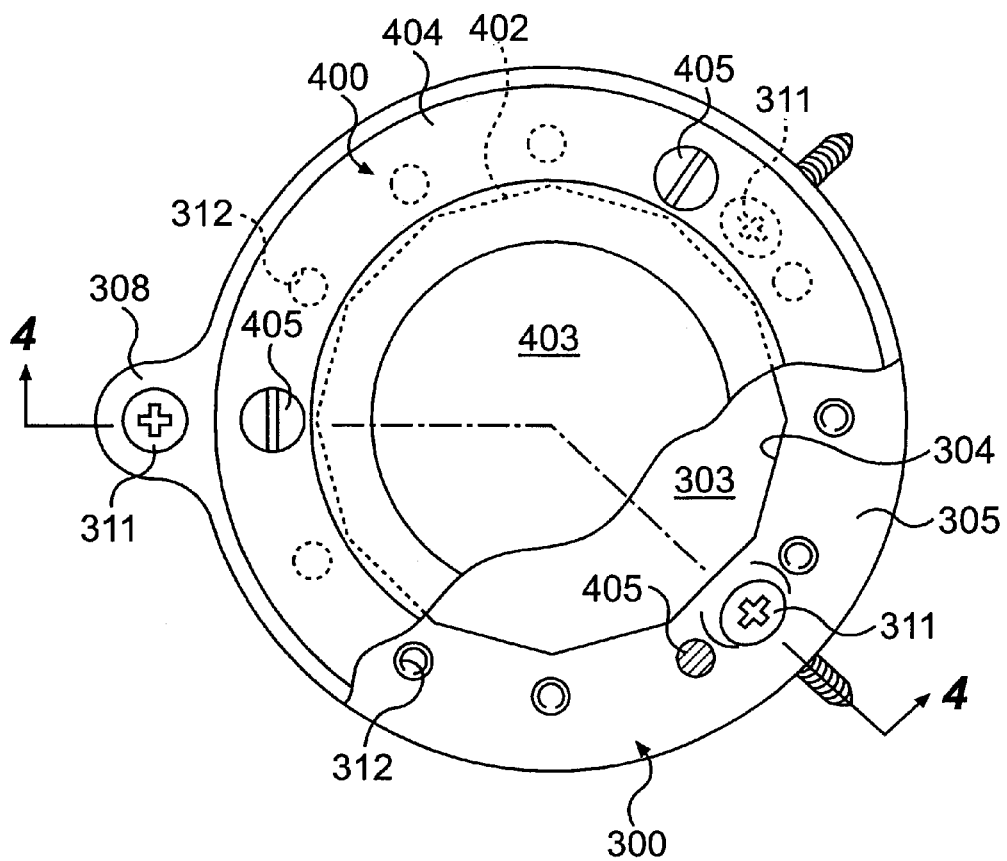
Figure 4:
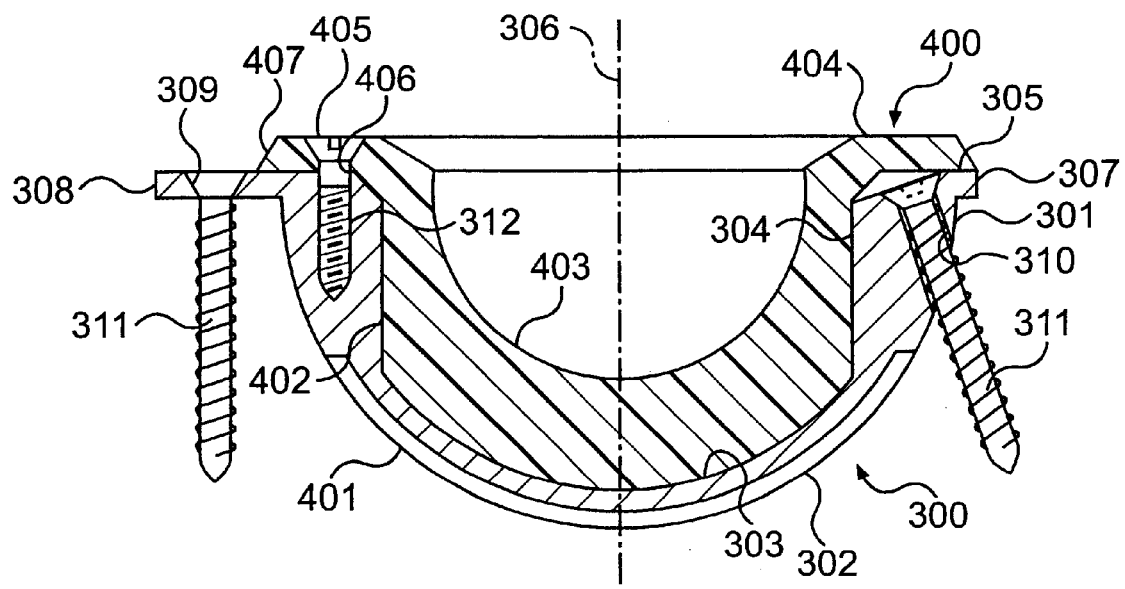
Figure 5:
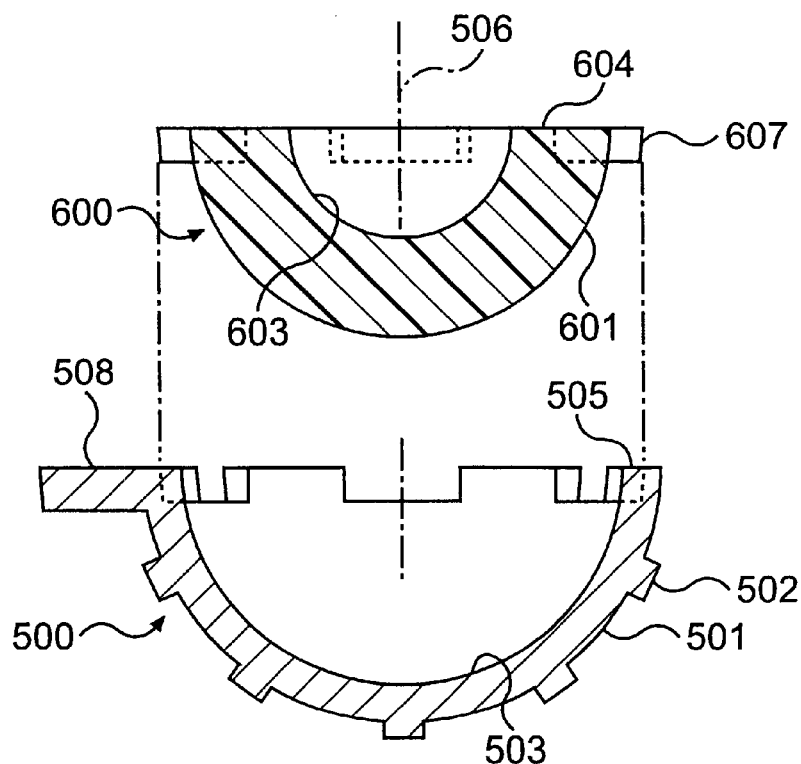
Figure 6:
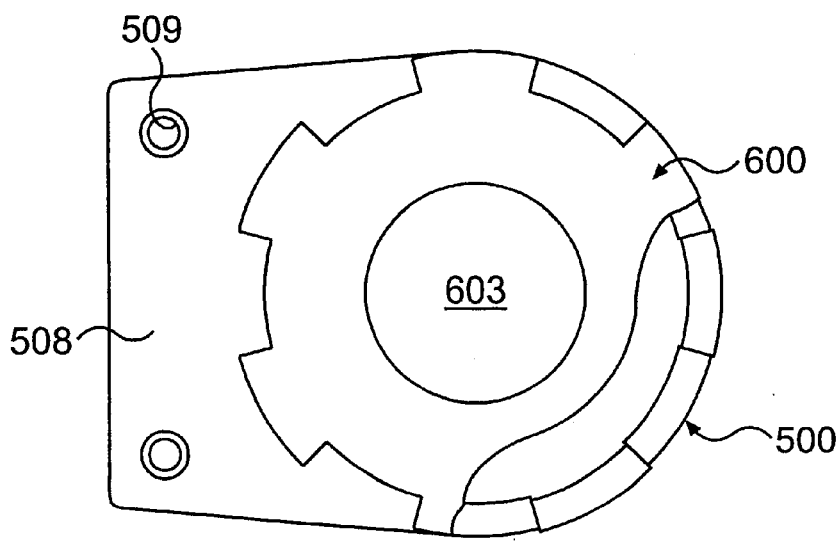

In order that the invention may be clearly understood and readily carried into effect, it will now be more fully described, by way of example, with reference to the accompanying drawings in which:

FIGS. 1 and 2 respectively illustrate in plan and cross-sectional views one embodiment of an acetabular cup component according to the present invention;

FIGS. 3 and 4 similarly illustrate a further such embodiment, but with the inner component part partially cut away plan view; and FIGS. 5 and 6 similarly illustrate another such embodiment, also with the inner part partially cut away in plan view and with the outer and inner parts disengaged in side view.

FIGS. 1 and 2 are in fact each in three parts (a), (b) and (c) illustrating the use of respectively different inner parts of a range thereof for connection with a common outer component part. Notwithstanding these differences, it is appropriate to employ common reference numerals throughout these figures.

The principal component parts, the outer and inner parts, are respectively denoted at 100 and 200 and each is of generally cup form.

The outer part 100 has a main exterior surface 101 which is basically spherically shaped, but is supplemented by the provision of raised portions 102, such as annular ribs, to form a relieved surface configuration. The interior surface of the part 100 has an innermost portion 103 which is spherically shaped concentrically with the exterior surface 101, and a remaining prismatically shaped portion 104 which extends to the rim surface 105 and is of regular polygonal cross-sectional shape.

The overall shaping of the outer part is symmetrical about the longitudinal axis 16 of the prismatic surface portion 104.

The inner part 200 has a main exterior surface with spherically and prismatically shaped portions 201 and 202 complementary to surface portions 103 and 104 of the outer part 100, whereby the inner part can be engaged in the outer part as shown. The remaining surface areas of the inner part comprise a substantially hemispherical interior surface 203 and rim surface 204, and these surfaces vary from one inner part to another within a range thereof.

These surface variations in the inner part involve, as noted above, two basic factors.

A first factor is that of the depth of the surface 203. There will normally be at least three positions, namely, a normal or standard one in which the surface 203 is typically concentric with the spherically shaped portion 201 of the exterior surface, and low and high positions in which the surface 203 is respectively more and less deeply located.

The second variant factor is that of the inclination of the surface 203 relative to the axis 106. Typically there can be five different angles such as 0°, 3°, 5°, 10° and 15°, or some other range up to a maximum of about 20°.

It will be appreciated that with variations such as just described there can be fifteen different inner parts to cater for different articulation requirements for a given outer part location in an individual pelvis. FIGS. 1 and 2 show at (a), (b) and (c) three examples of such parts, namely, standard depth at 0° or neutral inclination, low depth at 15° inclination, and high depth at 5° inclination. These examples also serve to show associated variations in the form of the rim surface 204.

It is to be noted that, in addition to these variations in inner part geometry, each such part can be located in as many different positions within the outer part as there are faces to the prismatic surface shaping at 104 and 202 simply by appropriate rotational positioning of the inner part during engagement with the outer part. This is-relevant, of course, to the inclined rather than the neutral inner parts. It is thought, at present, adequate to provide twelve rotational positions successively spaced by 30°.

Use of the embodiment of FIGS. 1 and 2 is largely self-evident from the foregoing description.

The outer part 100 is first secured in the acetabulum after suitable exposure and preparation of the bone, such securement taking the fullest account of the bone geometry and condition to ensure optimal engagement within sound bone material. In the present instance securement is to involve the currently conventional usage of bone cement as a gap-filling medium which forms a mechanical lock with the surface 101 and raised surface portions 102 on the one hand and with the pores of the prepared bone and cavities prepared therein on the other hand.

Thereafter the inner part 200 is selected which, when engaged in the secured outer part 100, is judged to have its surface 203 best located to serve the purposes of articulation in association with a femoral head replacement providing a ball complementary with the surface 203. This selection will involve consideration of the depth, inclination and rotation angle of the surface 203 and will normally be established by the use of trial inner parts which are readily engageable and withdrawable from the secured outer part. Once this selection is made, a replacement inner part of the corresponding configuration is secured in the outer part, suitably by press fitting.

The embodiment of FIGS. 3 and 4 is sufficiently similar in many respects to that just described, not least in the geometrical variations for the interior surface of the inner part, that it is only necessary for one example to illustrate the differences. Also, it is convenient to employ the same reference numerals for corresponding features between the two embodiments, but with increase of the hundreds digit to distinguish the second embodiment so that the outer and inner parts are respectively denoted as 300 and 400.

A first difference in FIGS. 3 and 4 is that securement of the outer part 300 does not rest on the use of bone cement alone, although a grooved structure, with ribs 302, is provided for this purpose over the lower part of the exterior surface 301. As an additional feature, the outer part rim is radially outwardly lipped at 307 and part of the lip continues into a lug 308 which is apertured at 309 to allow screw securement to underlying bone. Also, at locations opposed to the lug 308, the side wall of the outer part is obliquely bored at 310 from the rim to the exterior surface to allow additional screw securement to additional bone. In each case the screw-receiving bores are suitably counterbored and/or countersunk so that the heads of the associated screws 311 are not proud of the outer part rim.

A further difference is that the inner part 400 is secured to the outer part by screws 405 in addition, or as an alternative, to press fitting. In this connection the outer part has circumferentially uniformly spaced tapped bores 312 around its rim, and the inner part has three similarly located countersunk bores 406 which register with bores 312 at any position of rotational adjustment. It will be noted that the inner part rim is lipped at 407 to overlie that of the outer part and to accomodate the bores 406.

The embodiment of FIGS. 5 and 6 also only requires one example to illustrate its different features and, conveniently again, the same reference numberal sequence is used but with the outer and inner parts respectively denoted as 500 and 600.

The main difference in this embodiment is the provision of mutually complementary castellated formations in the rim surface 505 of the outer part and in the rim lip 607 of the inner part. These formations are uniformly circumferentially distributed to allow rotationally selective engagement of the outer and inner parts in place of the prismatic surface portions of the previous embodiments. In the present case the interior and exterior surfaces 503 and 601 of the outer and inner parts can be wholly spherically shaped, as shown.

A further difference in this third embodiment is that the outer part has a lug 508 apertured at 509 for screw securement to bone, but the lug is widened relative to that of FIGS. 3 and 4.

While the invention has been described in more detail with reference to the illustrated examples, this is not intended to be exhaustive in respect of possible variations. There are in fact a number of facets of the invention where further variation is possible.

Securement of the outer cup is one such facet. Reference has already been made to the possiblity of using bone cement and/or screws, but use may be made of any other securement technique. One such technique can involve so-called in-growth by the use of porous or functionally equivalent formations into which fibrous material grows and then ossifies. Another possiblity contemplated for study in further development of the invention is that primary securement by screws or other force-fitted elements may be enhanced by the packing of bone chips or paste, suitably prepared from the patient's excised femoral head, to fill voids in the acetabular site and between it and the outer part. This last possiblity amounts in general terms to a bone grafting technique.

Also, in connection with securement of the outer part, variation can be exercised in respect of external shaping as is already evident from the variable provision of lugs and other elements. Another such variation contemplated for use with the invention is the provision of a transversely elongated ovalate shaping in place of the generally spherically shaped exterior surface to conform better to the natural acetabular shaping. The relevant ovalate shaping may reduce any tendency for migration of the component in the pelvis as is sometimes witnessed during revision surgery. Again, it is not essential for the purposes of the present invention that the outer part be wholly cup-shaped: a generally annular form may suffice.

Another facet open to considerable variation in detail is the adaptation for, and the mode of, interconnection between the outer and inner parts. Alternatives in adaptation are already evident from the examples of prismatic and castellated surface formations, but many other possibilities exist for suitable indented/detented formations. It will generally be appropriate to deploy any such formations uniformly circumferentially, but this is not essential. Thus, it can be adequate to provide a discrete rotational adjustment capability over less than 360° for situations where the overall orientation of the component is predictable in general terms, such predictably resulting, for example, from the use of an ovalate exterior shaping. Again, it is not essential that the outer and inner parts inherently comprise mutually complementary formations: for example the embodiment of FIGS. 3 and 4 could be rotatably adjustably connected by way of the outer part bores 312 and the co-operating screws 405 passing through the outer part.

Regarding the mode of interconnections: reference has been made to press fitting, but screw interconnection is also shown, as just mentioned, and another possibility can involve the use of a thin layer of bone cement on other bonding or gap-filling material. However, whatever the mode of interconnections, it is desirable that the inner part should be separable without undue difficulty, while leaving the outer part intact and secured to bone, against a possible future need for revision.

A further facet involves the position of the articulation surface of the inner part. As so far described in the illustrated embodiments this location is, even allowing for any inclination, generally central to the extent that the spherical centre of the relevant surface lies on the axis 106, 306 or 506. However, as an alternative, this centre can be translated from the axis in order to provide an increased wall thickness along the main line of load in use and, again, the preferred rotational adjustment facility has relevance to this feature.

Yet another facet for variation lies in the choice of materials for the device. On the basis of the materials most commonly used at present in endoprosthetic bone joint devices it is preferred that the outer and inner parts respectively be of metal such as stainless steel, chrome-cobalt alloy or titanium alloy, and plastics material such as ultra high molecular weight polyethylene. Such a combination will provide stable securement to bone and low friction articulation with an associated metal femoral component. However other materials such as cermaics are in current usage, and others are under trial and development, so that various suitable choices will be possible.

What is claimed is:

1. A prosthesis assembly for replacement of an acetabulum, comprising:
   a supply including a plurality of bearing elements;
   an outer member having an external surface adapted for securement to bone and an internal engagement surface shaped to receive a bearing element selected from said supply of bearing elements;
   each bearing element having an exterior engagement surface for engagement with said internal engagement surface of said outer member;
   each bearing element having an interior surface shaped to engage a femoral head in a non-captive manner; and
   each bearing element having a rim surface, the rim surface of each bearing element having a different form from the rim surface of another bearing element of the supply.

2. A prosthesis assembly of claim 1, wherein the outer member includes a rim surface and wherein a geometrical relationship between the rim surface of the outer member and the rim surface of each bearing element when positioned in the outer member vary among the bearing elements of the supply.

3. A prosthesis assembly of claim 2, wherein the rim surface of at least one bearing element of the supply is inclined relative to the rim surface of the outer member.

4. A prosthesis assembly of claim 2, wherein the rim surface of at least one bearing element of the supply is at a different distance from the rim surface of the outer member in one region thereof than in another region thereof.

5. A prosthesis assembly of claim 1, wherein the interior surface of at least one bearing element in the supply of bearing elements has a different depth relative to the interior surface of another bearing element of the supply.

6. A prosthesis assembly of claim 1, wherein each bearing element from the supply is engageable in the outer member in a plurality of positions, said positions being angularly displaced from each other.

7. A prosthesis assembly of claim 1, wherein said positions of each bearing element in the outer member are defined by complementary formations on the bearing element and outer member.

8. A prosthesis assembly of claim 1, further comprising a plurality of outer members having different external surface characteristics for securement to bone.

9. A prosthetic joint system, comprising:
   a femoral head;
   an outer member having an external surface adapted for securement to bone and an internal engagement surface shaped to receive a bearing element selected from a supply of bearing elements;
   each bearing element having an exterior engagement surface for engagement with said internal engagement surface of said outer member;
   each bearing element having an interior surface shaped to engage the femoral head in a non-captive manner; and
   each bearing element having a rim surface, the rim surface of each bearing element having a different form from the rim surface of another bearing element of the supply.

10. A prosthetic joint system of claim 9, wherein the outer member includes a rim surface and wherein a geometrical relationship between the rim surface of the outer member and the rim surface of each bearing element supply when positioned in the outer member vary among the bearing elements of the supply.

11. A prosthetic joint system of claim 10, wherein the rim surface of at least one bearing element of the supply is inclined relative to the rim surface of the outer member.

12. A prosthetic joint system of claim 10, wherein the rim surface of at least one bearing element of the supply is at a different distance from the rim surface of the outer member in one region thereof than in another region thereof.

13. A prosthetic joint system of claim 9, wherein the interior surface of at least one bearing element in the supply of bearing elements has a different depth relative to the interior surface of another bearing element of the supply.

14. A prosthetic joint system of claim 9, wherein each bearing element from the supply is engageable in the outer member in a plurality of positions, said positions being angularly displaced from each other.

15. A prosthetic joint system of claim 9, wherein said positions of each bearing element in the outer member are defined by complementary formations on the bearing element and outer member.

16. A prosthetic joint system of claim 9, further comprising a plurality of outer members having different external surface characteristics for securement to bone.

17. A method for replacing an acetabulum in hip joint surgery, comprising:
 providing an outer member having an internal engagement surface adapted to engage an exterior surface of a bearing element;
 providing a supply of bearing elements suitable for engagement with said outer member, each bearing element of said supply having an interior surface shaped to engage with a femoral head in a non-captive manner, and each bearing element in said supply having a rim surface, the rim surface of each bearing element having a different form from the rim surface of another bearing element of the supply;
 securing said outer member to a patient's bone;
 selecting a bearing element from said supply deemed to best suit the patient; and
 fixing said selected bearing element into said outer member.

18. A replacement method of claim 17, wherein the outer member includes a rim surface and wherein a geometrical relationship between the rim surface of the outer member and the rim surface of each bearing element when positioned in the outer member vary among the bearing elements of the supply.

19. A replacement method of claim 18, wherein the rim surface of at least one bearing element of the supply is inclined relative to the rim surface of the outer member.

20. A replacement method of claim 18, wherein the rim surface of at least one bearing element of the supply is at a different distance from the rim surface of the outer member in one region thereof than in another region thereof.

21. A replacement method of claim 17, wherein the interior surface of at least one bearing element in the supply of bearing elements has a different depth relative to the interior surface of another bearing element of the supply.

22. A replacement method of claim 17, wherein each bearing element from the supply is engageable in the outer member in a plurality of positions, said positions being angularly displaced from each other.

23. A replacement method of claim 17, wherein said positions of each bearing element in the outer member are defined by complementary formations on the bearing element and outer member.

24. A replacement method of claim 17, further comprising providing a plurality of outer members having different external surface characteristics for securement to bone.

25. A method for implanting a prosthetic joint system, comprising:
 providing a femoral head;
 providing an outer member having an internal engagement surface adapted to engage an exterior surface of a bearing element;
 providing a supply of bearing elements suitable for engagement with said outer member, each bearing element of said supply having an interior surface shaped to engage with said femoral head in a non-captive manner, and each bearing element in said supply having a rim surface, the rim surface of each bearing element having a different form from the rim surface of another bearing element of the supply;
 securing said outer member to a patient's bone;
 selecting a bearing element from said supply deemed to best suit the patient;
 fixing said selected bearing element into said outer member; and
 engaging the femoral head with said selected bearing element.

26. A method of implantation of claim 25, wherein the outer member includes a rim surface and wherein a geometrical relationship between the rim surface of the outer member and the rim surface of each bearing element when positioned in the outer member vary among the bearing elements of the supply.

27. A method of implantation of claim 26, wherein the rim surface of at least one bearing element of the supply is inclined relative to the rim surface of the outer member.

28. A method of implantation of claim 26, wherein the rim surface of at least one bearing element of the supply is at a different distance from the rim surface of the outer member in one region thereof than in another region thereof.

29. A method of implantation of claim 25, wherein the interior surface of at least one bearing element in the supply of bearing elements has a different depth relative to the interior surface of another bearing element of the supply.

30. A method of implantation of claim 25, wherein each bearing element from the supply is engageable in the outer member in a plurality of positions, said positions being angularly displaced from each other.

31. A method of implantation of claim 25, wherein said positions of each bearing element in the outer member are defined by complementary formations on the bearing element and outer member.

32. A method of implantation of claim 25, further comprising providing a plurality of outer members having different external surface characteristics for securement to bone.

* * * * *